United States Patent [19]

Srivastava et al.

[11] Patent Number: 6,114,514
[45] Date of Patent: Sep. 5, 2000

[54] *MYCOBACTERIUM TUBERCULOSIS* SPECIFIC DNA FRAGMENT

[75] Inventors: Ranjana Srivastava; Deepak Kumar; Brahm Shanker Srivastava, all of Lucknow, India

[73] Assignee: Council of Scientific & Industrial Research, New Delhi, India

[21] Appl. No.: 08/997,897

[22] Filed: Dec. 24, 1997

[51] Int. Cl.[7] .......................... C07H 21/02; C07H 21/04; A61K 39/40; C12N 1/12
[52] U.S. Cl. .................. 536/23.1; 424/168.1; 424/248.1; 435/253.1; 536/23.7; 536/24.3; 536/24.32
[58] Field of Search .............................. 424/168.1, 248.1; 435/253.1; 536/23.1, 23.7, 24.3, 24.32

[56] References Cited

U.S. PATENT DOCUMENTS 5,370,998  12/1994  Crawford et al. ...................... 435/91.2

OTHER PUBLICATIONS

Kiehn, T.E., Clinical Infectious Diseases, 17 (Supp 2), 1:S447–S454, (1993).

*Primary Examiner*—Rodney P. Swartz
*Attorney, Agent, or Firm*—Ladas & Parry

[57] ABSTRACT

This invention relates to a *Mycobacterium tuberculosis* specific DNA fragment containing IS like and repetitive sequences, a method of production of such DNA fragment and the use of such DNA fragment, for example, to rapidly diagnose *Mycobacterium tuberculosis* infection in clinical samples, and to identify clinical isolates of *Mycobacterium tuberculosis*. The DNA fragment may be used to determine information about the epidemiology of *Mycobacterium tuberculosis* infection.

5 Claims, 11 Drawing Sheets

Figure 9

```
5'        10         20         30         40         50         60
      AGGCCTCGGT GACCGTGATC ATGTTGCCGC CGAAGGTCAT TACGTTGTGT ACGTCAATGA
          70         80         90        100        110        120
      CCATCTGCTC GTTGTTTATG GGGATGAATC GGGAGTGGTG ACCGAGAGAT CGATGGCGAA
         130        140        150        160        170        180
      TCTGGCCCTG GTTATCGCCC GCCACCAAGA AGCCATTGTT GAAGTCGCCC GTGTCGAAAG
         190        200        210        220        230        240
      CGCCGGTATT GACGTTGCCG GGATTGAAGA AGCCGGTGTT GGTGTCACCC GGGTTATAGC
         250        260        270        280        290        300
      TGCCGGTATT GGTGTCACCC ACGTTGAAGT TGCCGGTGTT GGTGTTACCG ACGTTGAAGC
         310        320        330        340        350        360
      CGCCGGTGTT GTAGCTGCCC GTGTTGTAGA AGCCCGTGTT GAAGTCGCCG GCGTTGAGGA
         370        380        390        400        410        420
      TGCCCGTGTT GTAGCTGCCA GCATTGAGGA TGCCGGTATT GTCGGTACCC GGGTTCCCGA
         430        440        450        460        470        480
      TACCCCAGTT CCCGGTGCCC GAGTTTGCGA TGCCGACGTT TCCGGTGCCC GCGTTGAAGA
         490        500        510        520        530        540
      TGCCAACGTT ATTGGTGCCC GAATTGAACA GGCCGCTGTT GCCGGTGCCC GAGTTCCAGC
         550        560        570        580        590        600
      CGCTAGCAAT ATTGAAGCCC TGCTGGTTGT CGCCGGACAG CCCGATGCCG ATGTTGTTGT
         610        620        630        640        650        660
      TGCCGGTGTT GGCGAACCCG ATGTTGTTGT TGCCGGTGTT GGCAAAGCCT TGGTTGAAGT
         670        680        690        700        710        720
      CGCCCGCGTT CCCGAAGCCG ACGTTGTAGT CGCCGACGTT TCCAAAACCG ATGTTGTAGA
         730        740        750        760        770        780
      TCCCGAGGTT TCCGGATCCG ATGTTGTAGT TTCCCAGGCT TCCGGAACCG ACATTGAATAA
         790        800        810        820        830        840
      CTCCGATGTT TCCACTGCCG ATATTGAAGC TGCCGACGTT GCCGCTGCCC AAGATGTTTT
         850        860        870        880        890        900
      GGCTGCCGAG GTTGCCGCTG CCAAGGATGT TGAAGTCACC GACGTTTCCG CTGCCGAGAA
         910        920        930        940        950        960
      TGTTGTAATT GCCGATGTTG GCGTTCCGA  GAATGTTCAC GACGCCCGG  TTTGCCAGGC
         970        980        990       1000       1010       1020
      CGAGATTGAA GACCGGTGGG CCACCGAAAA ATCCCGACAT GTTGCTTCCG GTGTTGAAGA
        1030       1040       1050       1060       1070       1080
      AGCCCGAGAT CAAGGCCGGC GTTGTGATGG CCACCAGGCT CATGTTGAAC AAACCCGATA
        1090       1100       1110       1120       1130       1140
      CGGTGTTGCC CGAGTTGATC ACGCCCGATA CCAGCACGCC CGCGTTTGCC AGGCCGGAGT
        1150       1160       1170       1180       1190       1200
      TACCGATGGCC CCCCGACGAA GAGTGGAAGA AGCCAGAATT GTTGGCACCG GAGTTCAGGA
        1210       1220       1230       1240       1250       1260
      AGCCGGACGC GCTACCGGCA CCGCTGTTGA AGAATCCCGA CGACGGCGCA CTGGTCGAGT
        1270       1280       1290
      TGAAGAAGCC GGGCTCCCGA AAATCAGGCC T   3'
```

Figure 10

Sequence Region: 1-1291
Translation Region: 1-1291

| Arg | Pro | Arg | *** | Pro | *** | Ser | Cys | Cys | Arg | Arg | Arg | Ser | Leu | Arg | Cys | 16 |
|---|---|---|---|---|---|---|---|---|---|---|---|---|---|---|---|---|
| ACG | CCT | CGG | TGA | CCG | TGA | TCA | TGT | TGC | CGC | CGA | AGG | TCA | TTA | CGT | TGT | 48 |

| Val | Arg | Gln | *** | Pro | Ser | Ala | Arg | Cys | Leu | Trp | Gly | *** | Ile | Gly | Ser | 32 |
|---|---|---|---|---|---|---|---|---|---|---|---|---|---|---|---|---|
| GTA | CGT | CAA | TGA | CCA | TCT | GCT | GCT | TGT | TTA | TGG | GGA | TGA | ATC | GGG | AGT | 96 |

| Gly | Asp | Arg | Glu | Ile | Asp | Gly | Glu | Ser | Gly | Pro | Gly | Tyr | Arg | Pro | Pro | 48 |
|---|---|---|---|---|---|---|---|---|---|---|---|---|---|---|---|---|
| GGT | GAC | CGA | GAG | ATC | GAT | GGC | GAA | TCT | GGC | CCT | GGT | TAT | CGC | CCG | CCA | 144 |

| Pro | Arg | Ser | His | Cys | *** | Ser | Arg | Pro | Cys | Arg | Lys | Arg | Arg | Tyr | *** | 64 |
|---|---|---|---|---|---|---|---|---|---|---|---|---|---|---|---|---|
| CCA | AGA | ACG | CAT | TGT | TGA | AGT | CGC | CCG | TGT | CGA | AAG | CGC | CGG | TAT | TGA | 192 |

| Arg | Cys | Arg | Asp | *** | Arg | Ser | Arg | Cys | Trp | Cys | His | Pro | Gly | Tyr | Ser | 80 |
|---|---|---|---|---|---|---|---|---|---|---|---|---|---|---|---|---|
| CGT | TGC | CGG | GAT | TGA | AGA | AGC | CGG | TGT | TGG | TGT | CAC | CCG | GGT | TAT | ACG | 240 |

| Cys | Arg | Tyr | Trp | Cys | His | Pro | Arg | *** | Ser | Cys | Arg | Cys | Trp | Cys | Tyr | 96 |
|---|---|---|---|---|---|---|---|---|---|---|---|---|---|---|---|---|
| TGC | CGG | TAT | TGG | TGT | CAC | CCA | CGT | TGA | AGT | TCG | CGG | TGT | TGG | TGT | TAC | 288 |

| Arg | Arg | *** | Ser | Arg | Arg | Cys | Cys | Ser | Cys | Pro | Cys | Cys | Arg | Ser | Pro | 112 |
|---|---|---|---|---|---|---|---|---|---|---|---|---|---|---|---|---|
| CGA | CGT | TGA | AGC | CGC | CGG | TGT | TGT | AGC | TCG | CCG | TGT | TGT | AGA | AGC | CCG | 336 |

| Cys | *** | Ser | Arg | Arg | Arg | *** | Gly | Cys | Pro | Cys | Cys | Ser | Cys | Gln | His | 128 |
|---|---|---|---|---|---|---|---|---|---|---|---|---|---|---|---|---|
| TGT | TGA | AGT | CGC | CGG | CGT | TGA | CCA | TGC | CCG | TGT | TGT | AGC | TGC | CAG | CAT | 384 |

| *** | Gly | Cys | Arg | Tyr | Cys | Arg | Tyr | Pro | Gly | Ser | Arg | Tyr | Pro | Ser | Ser | 144 |
|---|---|---|---|---|---|---|---|---|---|---|---|---|---|---|---|---|
| TGA | GGA | TGC | CGG | TAT | TGT | CGG | TAC | CCG | GGT | TCC | CGA | TAC | CCC | AGT | TCC | 432 |

| Arg | Cys | Pro | Ser | Leu | Arg | Cys | Arg | Arg | Phe | Arg | Cys | Pro | Arg | *** | Arg | 160 |
|---|---|---|---|---|---|---|---|---|---|---|---|---|---|---|---|---|
| CGG | TGC | CCG | AGT | TTG | CGA | TGC | CGA | CGT | TTC | CGG | TGC | CCG | CGT | TGA | AGA | 480 |

| Cys | Gln | Arg | Tyr | Trp | Cys | Pro | Asn | *** | Thr | Gly | Arg | Cys | Cys | Arg | Cys | 176 |
|---|---|---|---|---|---|---|---|---|---|---|---|---|---|---|---|---|
| TGC | CAA | CGT | TAT | TGG | TGC | CCG | AAT | TGA | ACA | GGC | CGC | TGT | TCG | CGG | TGC | 528 |

| Pro | Ser | Ser | Ser | Arg | *** | Gln | Tyr | *** | Ser | Pro | Ala | Gly | Cys | Arg | Arg | 192 |
|---|---|---|---|---|---|---|---|---|---|---|---|---|---|---|---|---|
| CCG | AGT | TCC | AGC | CGC | TAG | CAA | TAT | TGA | AGC | CCT | GCT | GGT | TGT | CGC | CGG | 576 |

| Thr | Ala | Arg | Cys | Arg | Cys | Cys | Cys | Cys | Arg | Cys | Trp | Arg | Thr | Arg | Cys | 208 |
|---|---|---|---|---|---|---|---|---|---|---|---|---|---|---|---|---|
| ACA | GCC | CGA | TGC | CGA | TGT | TGT | TGT | TGT | CGG | TGT | TGG | CGA | ACC | CGA | TGT | 624 |

| Cys | Cys | Cys | Arg | Cys | Trp | Gln | Ser | Leu | Gly | *** | Ser | Arg | Pro | Arg | Ser | 224 |
|---|---|---|---|---|---|---|---|---|---|---|---|---|---|---|---|---|
| TGT | TGT | TGC | CGG | TGT | TGG | CAA | AGC | CTT | GGT | TGA | AGT | CGC | CCG | CGT | TCC | 672 |

| Arg | Ser | Arg | Arg | Cys | Ser | Arg | Arg | Arg | Phe | Gln | Asn | Arg | Cys | Cys | Arg | 240 |
|---|---|---|---|---|---|---|---|---|---|---|---|---|---|---|---|---|
| CGA | AGC | CGA | CGT | TGT | AGT | CGC | CGA | CGT | TTC | CAA | AAC | CGA | TGT | TGT | AGA | 720 |

| Ser | Arg | Gly | Phe | Arg | Ile | Arg | Cys | Cys | Ser | Phe | Pro | Gly | Phe | Arg | Asn | 256 |
|---|---|---|---|---|---|---|---|---|---|---|---|---|---|---|---|---|
| TCC | CGA | GGT | TTC | CGG | ATC | CGA | TGT | TGT | ACT | TTC | CCA | GGC | TTC | CGG | AAC | 768 |

| Arg | His | *** | Ile | Leu | Arg | Cys | Phe | His | Cys | Arg | Tyr | *** | Ser | Cys | Arg | 272 |
|---|---|---|---|---|---|---|---|---|---|---|---|---|---|---|---|---|
| CGA | CAT | TGA | ATA | CTC | CGA | TGT | TTC | CAC | TGC | CGA | TAT | TGA | AGC | TGC | CGA | 816 |

| Arg | Cys | Arg | Cys | Pro | Arg | Cys | Phe | Gly | Cys | Arg | Gly | Cys | Arg | Cys | Gln | 288 |
|---|---|---|---|---|---|---|---|---|---|---|---|---|---|---|---|---|
| CGT | TGC | CCG | TGC | CCA | AGA | TGT | TTT | GGC | TGC | CGA | GGT | TGC | CGC | TGC | CAA | 864 |

| Gly | Cys | *** | Ser | His | Arg | Arg | Phe | Arg | Cys | Arg | Glu | Cys | Cys | Asn | Cys | 304 |
|---|---|---|---|---|---|---|---|---|---|---|---|---|---|---|---|---|
| CCA | TGT | TGA | AGT | CAC | CGA | CGT | TTC | CGC | TGC | CGA | GAA | TGT | TGT | AAT | TGC | 912 |

| Arg | Cys | Trp | Arg | Cys | Arg | Glu | Cys | Ser | Arg | Arg | Pro | Gly | Leu | Pro | Gly | 320 |
|---|---|---|---|---|---|---|---|---|---|---|---|---|---|---|---|---|
| CGA | TGT | TGG | CGT | TGC | CGA | GAA | TGT | TCA | CGA | CGC | CCC | GGT | TTG | CCA | CGC | 960 |

Figure 10 (from previous page)

| | | | | | | | | | | | | | | | | |
|---|---|---|---|---|---|---|---|---|---|---|---|---|---|---|---|---|
| Arg | Cys | *** | Arg | Ser | Pro | Arg | Ser | Arg | Pro | Ala | Leu | *** | Trp | Pro | Pro | 352 |
| CGG | TGT | TGA | AGA | AGC | CCG | AGA | TCA | AGG | CCG | GCG | TTG | TGA | TGG | CCA | CCA | 1056 |
| Gly | Ser | Cys | *** | Thr | Asn | Pro | Ile | Arg | Cys | Cys | Pro | Ser | *** | Ser | Arg | 368 |
| GGC | TCA | TGT | TGA | ACA | AAC | CCG | ATA | CGG | TGT | TGC | CCG | AGT | TGA | TCA | CGC | 1104 |
| Pro | Ile | Pro | Ala | Arg | Pro | Arg | Leu | Pro | Gly | Arg | Ser | Tyr | Arg | Trp | Pro | 384 |
| CCG | ATA | CCA | GCA | CGC | CCG | CGT | TTG | CCA | GGC | CGG | AGT | TAC | CGA | TGG | CCC | 1152 |
| Pro | Thr | Lys | Ser | Gly | Arg | Ser | Gln | Asn | Cys | Trp | His | Arg | Ser | Ser | Gly | 400 |
| CCG | ACG | AAG | AGT | GGA | AGA | AGC | CAG | AAT | TGT | TGG | CAC | CGG | AGT | TCA | GGA | 1200 |
| Ser | Arg | Thr | Arg | Tyr | Arg | His | Arg | Cys | *** | Arg | Ile | Pro | Thr | Thr | Ala | 416 |
| AGC | CGG | ACG | CGC | TAC | CGG | CAC | CGC | TGT | TGA | AGA | ATC | CCG | ACG | ACG | GCG | 1248 |
| His | Trp | Ser | Ser | *** | Arg | Ser | Arg | Ala | Pro | Glu | Asn | Gln | Ala | | | 430 |
| CAC | TGG | TCG | AGT | TGA | AGA | CGG | GCT | CCC | GAA | AAT | CAG | GCC | T | | | 1291 |

MYCOBACTERIUM TUBERCULOSIS SPECIFIC DNA FRAGMENT

FIELD OF INVENTION

This invention relates to a *Mycobacterium tuberculosis* specific DNA fragment containing IS like and repetitive sequences, a method of production of such DNA fragment and the use of such DNA fragment, for example, to rapidly diagnose *Mycobacterium tuberculosis* infection in clinical samples, and to identify clinical isolates of *Mycobacterium tuberculosis*. The DNA fragment may be used to determine information about the epidemiology of *Mycobacterium tuberculosis* infection. Specifically this invention relates to the use of sequence specific DNA fragments to diagnose *Mycobacterium tuberculosis* and strains of *Mycobacterium tuberculosis*. A purpose of the study of the epidemiology of tuberculosis is to distinguish the genetic diversity of the causative agent *Mycobacterium tuberculosis* and to obtain information about strain to strain variability. This can be achieved by molecular epidemiological methods including DNA fingerprinting and restriction fragment length polymorphism (RFLP) analysis. Such approaches, can aid the investigation of point source outbreaks, transmission, pathogenesis and may be employed as a marker of strain typing.

BACKGROUND OF THE INVENTION

Tuberculosis (TB) is a major cause of infectious mortality. According to a recent WHO report, the number of deaths attributed to TB was a larger number in 1995 than in any other year in history (Moran, N. 1996. WHO Issues Another Gloomy Report. Nature Medicine 4:377). Tuberculosis remains widespread worldwide and constitutes a major health problem particularly in developing countries. One third of the total world's population (nearly two billion people) is infected with *Mycobacterium tuberculosis* out of which 5 to 10% develop the disease. TB causes more than 3 million deaths per year and recently WHO has predicted that 30 million people will die of TB in the next ten years (Joint International Union Against Tuberculosis and World Health Organization Study Group. Tubercl 63:157–169, 1982).

Tuberculosis is caused by a gram positive acid fast bacterium *Mycobacterium tuberculosis* or *M. bovis*, which are the tubercle bacilli of the family of Mycobacteriaceae. *M. bovis* is a species which causes tuberculosis in cattle and can be transmitted to humans and other animals in which it causes tuberculosis. At present nearly all tuberculosis in humans is caused by *Mycobacterium tuberculosis*. Infections occasionally result from other species of mycobacteria that are common environmental saprophytes. These species have been collectively termed as MOTT (Mycobacteria other than typical tubercle), environmental or tuberculoid bacilli. The difference between the two infections is that infection with *Mycobacterium tuberculosis* is always transmitted from host to host. In contrast, human beings infected with other mycobacteria rarely transmit the disease.

Hence the essential component of any tuberculosis control program is containment of the disease. Identification of infected individuals, especially those most likely to transmit viable bacilli, comes as a first priority in strategies for tuberculosis control. Early and timely diagnosis of tuberculosis is essential for identifying individuals carrying the bacilli. Therefore a need has arisen for a method of diagnosis of tuberculosis which is rapid, sensitive and specific. Routine diagnostic methods used for identification of *Mycobacterium tuberculosis* includes acid fast smear test in clinical samples like sputum, tests based on growth of bacilli in specific media and differential biochemical tests. The culture of mycobacteria from clinical samples is the most reliable and provides for definite diagnosis of tuberculosis. Although 100% specific, it takes six to eight weeks due to slow growth of organisms and further biochemical testing before identification can be made (Heifests, L. B. and Good, R. C. 1994. Current Laboratory Methods for the Diagnosis of Tuberculosis. Tuberculosis Pathogenesis, Protection and Control (ed. B. R. Bloom) ASM Washington DC, pp. 85–110).

Methods based on antigen and antibody detection in body fluids and more recently nucleic acid probes (sequence specific DNA fragments) have been developed as reagents for rapid diagnosis and monitoring of the epidemiology of tuberculosis (Young, D. B. and Mehlert, A. 1989, Serology of Mycobacteria: Characterization of Antigens Recognized by Monoclonal Antibodies. Rev. Infec. Dis. 12:S431-S435; Pfyfer, G. E., Kisling, P., Jahn, E. M. I., Martin, H., Salfinger; W. M. and Weber, R. 1996. Diagnostic Performance of Amplified *Mycobacterium Tuberculosis* Direct Test with Cerebrospinal Fluid, Other Non Respiratory and Respiratory Specimens, J. Clin. Microbiol. 34:834–841).

The DNA probes utilize a wide array of sequences from *Mycobacterium tuberculosis* ranging from whole genomic DNA, to a single copy sequence, and to repetitive DNA elements. When evaluated directly on clinical samples they have proved to be highly specific, sensitive and dramatically reduce the time for diagnosis of tuberculosis (Kiehn, T. E. 1993. The Diagnostic Mycobacteriology Laboratory of the 1990's. Clin. Infect. Dis. 17 (suppl.2) S447–S454).

Several sequence specific probes have been used as targets for identification of *Mycobacterium tuberculosis* by amplification of specific sequences by PCR.

IS6110 is an IS element present in members of *Mycobacterium tuberculosis* complex (*Mycobacterium tuberculosis, M. bovis, M. africanum,* and *M. microti*).

Different regions of IS6110 have been amplified using different sets of primers for PCR based diagnosis like 123 base pair (bp) or 245 bp region (Einsenach, K. D., Cave, M. D., Bates, J. H. and Crawford, J. T. 1990. Polymerase chain reaction amplification of repetitive DNA sequence specific for *Mycobacterium tuberculosis*. J. Infect. Dis. 161:977–981; Kolk, A. H. J., Schuitema, A. R. J., Kuijper, S., VanLeeuwen J., Hermans, P. W. M., Van Embden, J. D. A. Hartskeerl, R. A. 1992, Detection of *Mycobacterium tuberculosis* in clinical samples by using polymerase chain reaction and a non radioactive detection system. J. Clin. Microbiol. 30:2567–2575).

IS6110 has some disadvantages. Several *Mycobacterium tuberculosis* strains with one copy or no copy of IS6110 have been reported (Sahadevan, R., Narayanan, S. Paramsivam, C. N., Prabhakar, R. and Narayanan, P. R. 1995. Restriction fragment length polymorphism typing of clinical isolates of *Mycobacterium tuberculosis* from patients with pulmonary tuberculosis in Madras, India by use of direct repeat probe.

J. Clin. Microbiol. 33:3037–3039: Van Soolingen, D., Dehass, P. E. W., Hermans, P. W. M. Groenen, P. M. A. and Van Embden, J. D. A. 1993. Comparison of various repetitive DNA elements as genetic markers for strain differentiation and epidemiology of *Mycobacterium tuberculosis*. J. Clin. Microbiol. 31: 1987–1995). Thus the repertoire of *Mycobacterium tuberculosis* strains present all over the world may not be selected/amplified using a single repetitive element or one DNA probe specific to *Mycobacterium tuberculosis*. The search for newer DNA probes is a constant requirement.

OBJECTS OF THE INVENTION

It is an object of this invention to detect *Mycobacterium tuberculosis* in a clinical sample.

It is another object of this invention to describe a DNA fragment containing IS like sequence and repetitive sequences.

It is a further object of this invention to use a DNA fragment containing IS like sequence and repetitive sequences to detect *Mycobacterium tuberculosis*.

It is yet another object of this invention to describe a method for production of a DNA fragment containing IS like sequence and repetitive sequences.

It is another object of this invention to use a 1291 base pair sequence having an IS like sequence and repetitive sequences or a portion or fragment of the 1291 base pair sequence to detect *Mycobacterium tuberculosis*.

It is a further object of this invention to construct a sequence specific DNA probe for the identification of *Mycobacterium tuberculosis* present in clinical samples.

It is another object of this invention to develop a sequence specific DNA probe for identification of clinical isolates of *Mycobacterium tuberculosis* in order to distinguish it from other mycobacteria which may be present in the clinical samples.

It is yet another object of this invention to provide a sequence specific DNA probe for monitoring the epidemiology of tuberculosis.

It is further object of this invention to provide a sequence specific DNA probe for the detection of polymorphism in clinical isolates of *Mycobacterium tuberculosis*.

It is still another object of this invention to provide an IS element for transposition, mutagenesis and gene inactivation in mycobacteria for the investigation of pathogenesis, virulence and vaccine development.

SUMMARY OF THE INVENTION

This invention relates to *Mycobacterium tuberculosis* specific DNA fragment containing IS like sequence and repetitive sequences, a method of production of such DNA fragment and the use of such DNA fragment, for example, to rapidly diagnose *Mycobacterium tuberculosis* infection in clinical samples, to identify clinical isolates of *Mycobacterium tuberculosis* and to track the epidemiology of *Mycobacterium tuberculosis* infection. Specifically this invention relates to the use of sequence specific DNA fragment to diagnose tuberculosis and strains of *Mycobacterium tuberculosis*. The *Mycobacterium tuberculosis* specific DNA fragment consists of 1291 base pair (bp) sequence which contains an IS like element and several repeat DNA sequences.

When this DNA fragment is incubated with clinical samples which may contain mycobacteria of interest, the presence of *Mycobacterium tuberculosis* can be detected by specificity of hybridization. The DNA primers designed from the nucleotide sequence of this 1291 bp fragment may be incubated with clinical samples to amplify the DNA of *Mycobacterium tuberculosis* present in the clinical samples. Hence if the samples contain *Mycobacterium tuberculosis* it may be diagnosed specifically. The DNA fragment when hybridized with genomic DNA of clinical isolates of *Mycobacterium tuberculosis* by Southern hybridization, specifically hybridizes with *Mycobacterium tuberculosis* isolates and displays polymorphism. Hence, the fragment can be used in the specific diagnosis of *Mycobacterium tuberculosis* infections and to determine information about the epidemiology of *Mycobacterium tuberculosis* infections.

Mycobacteria can be detected in samples of sputum, cerebrospinal fluid, pleural fluid, urine, ascitic fluid, gastric samples, bronchial lavage, pericardial fluid, pus or lymph node aspirate.

One way to produce the *Mycobacterium tuberculosis* specific DNA fragment of the invention, is to use a genomic library of *Mycobacterium tuberculosis* DNA which may be constructed in a plasmid or phage lambda gt11 vector. The library of the genomic DNA fragments may be screened with genomic DNA of *Mycobacterium tuberculosis* as a probe to select the fragments which rapidly hybridize to *Mycobacterium tuberculosis* genomic DNA.

The detection of positive hybridization signals within 60 minutes may indicate that the clones may contain repeat sequences in the DNA fragment of *Mycobacterium tuberculosis*.

The clones thus obtained may further be screened by DNA-DNA hybridization with genomic DNA of mycobacteria other than *Mycobacterium tuberculosis* used as probes. The clones not producing any hybridization signals may be selected as containing *Mycobacterium tuberculosis* specific DNA fragments.

The DNA fragment of this invention may be used by incubating it with samples which may contain the specific mycobacteria of interest (*Mycobacterium tuberculosis*). If *Mycobacterium tuberculosis* is present, then the DNA fragment will hybridize with the DNA of *Mycobacterium tuberculosis* which can be detected for example by dot blot or Southern hybridization assay.

The nucleotide sequence of the specific DNA fragment may be determined and DNA primers may be designed for specific amplification of *Mycobacterium tuberculosis* DNA. The specific DNA primers may be added into the clinical samples to amplify *Mycobacterium tuberculosis* DNA if present in the sample. The amplified product may be visualized by for example agarose gel electrophoresis and hybridization with the specific DNA fragment of the invention. The polymerase chain reaction (PCR) amplification as well as hybridization with the specific DNA fragment of the invention may indicate that the sample contains *Mycobacterium tuberculosis* and hence may be used in detection and diagnosis of tuberculosis. By hybridization with the specific DNA fragment of the invention, epidemiology of tuberculosis and Mycobacterium tuberculosis may be traced as the fragment contains several repeat sequences and thus strain polymorphism of Mycobacterium tuberculosis may be determined.

BRIEF DESCRIPTION OF THE DRAWINGS

FIG. 9. Nucleotide sequence of the 1291 bp StuI-StuI fragment of Mycobacterium tuberculosis.

FIG. 10. Deduced amino acid sequence from the nucleotide sequence (as in FIG. 9) of 1291 bp StuI-StuI DNA fragment of Mycobacterium tuberculosis.

DETAILED DESCRIPTION OF THE INVENTION

Figure 1:
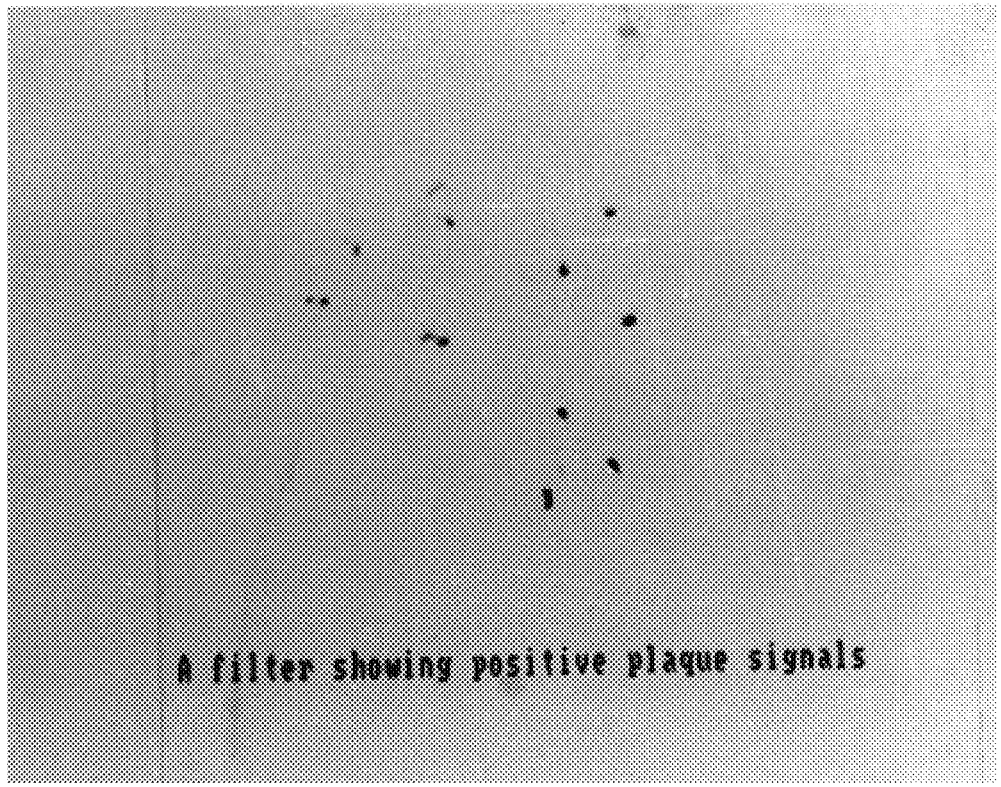
FIG. 1. Screening of recombinant lambda gt11 library of Mycobacterium tuberculosis with DIG-labeled denatured genomic DNA of Mycobacterium tuberculosis by DNA hybridization. Positive plaques gave hybridization signals within 60 min and appeared blue in color.
Figure 2:
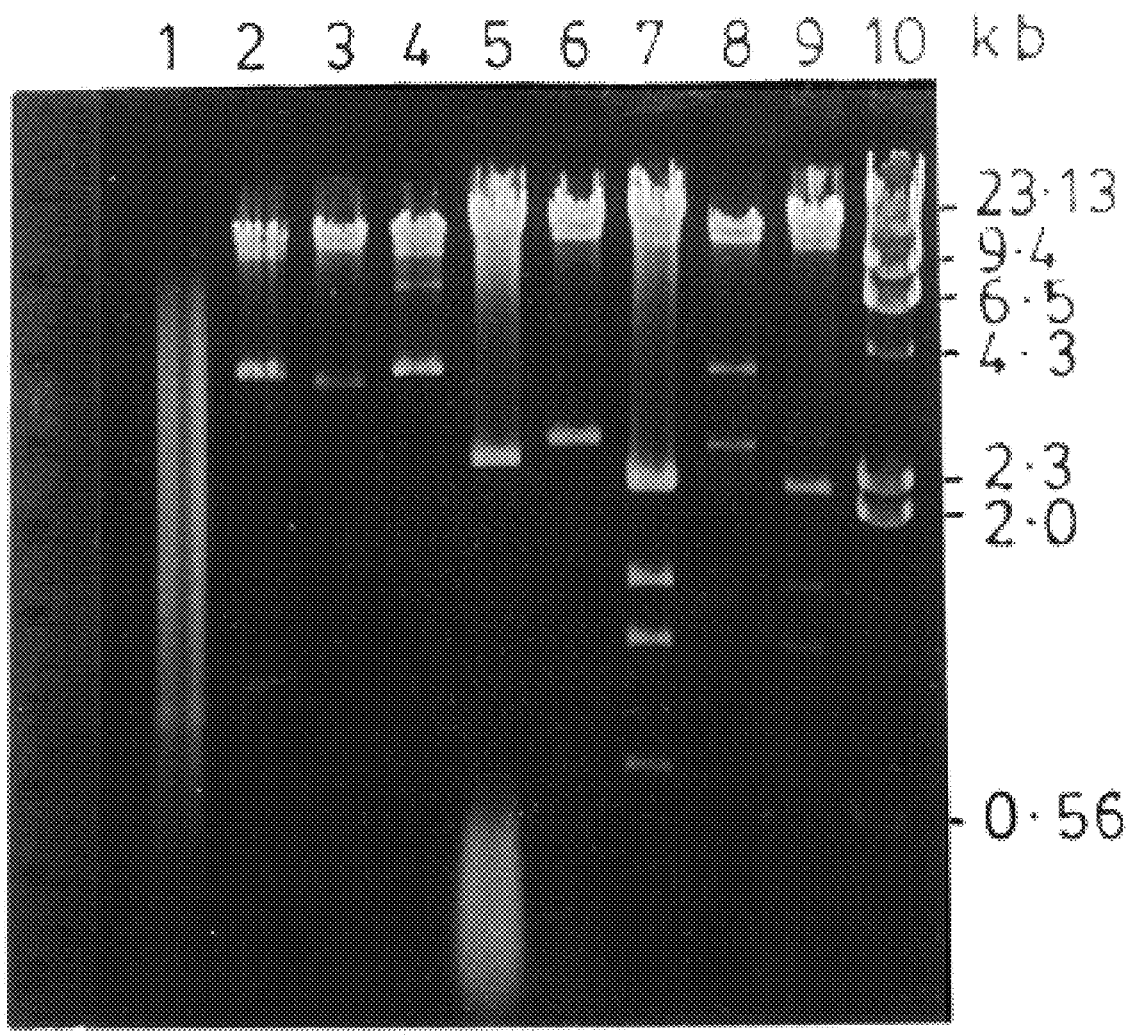
FIG. 2. Agarose (1%) gel electrophoresis analysis of EcoRI digests of recombinant lambda clones. The DNA from recombinant phages was isolated, digested with EcoRI restriction enzyme and electrophoresed. Lambda HinDIII (BRL) was used a molecular weight marker. Lane 2: Clone C8; Lane 3: Clone C10; Lane 4: Clone C16; Lane 5: Clone C33; Lane 6: Clone C38; Lane 7: Clone C41; Lane 8: Clone C60; Lane 9: Clone C70; Lane 10: Lambda HindIII.
Figure 3:
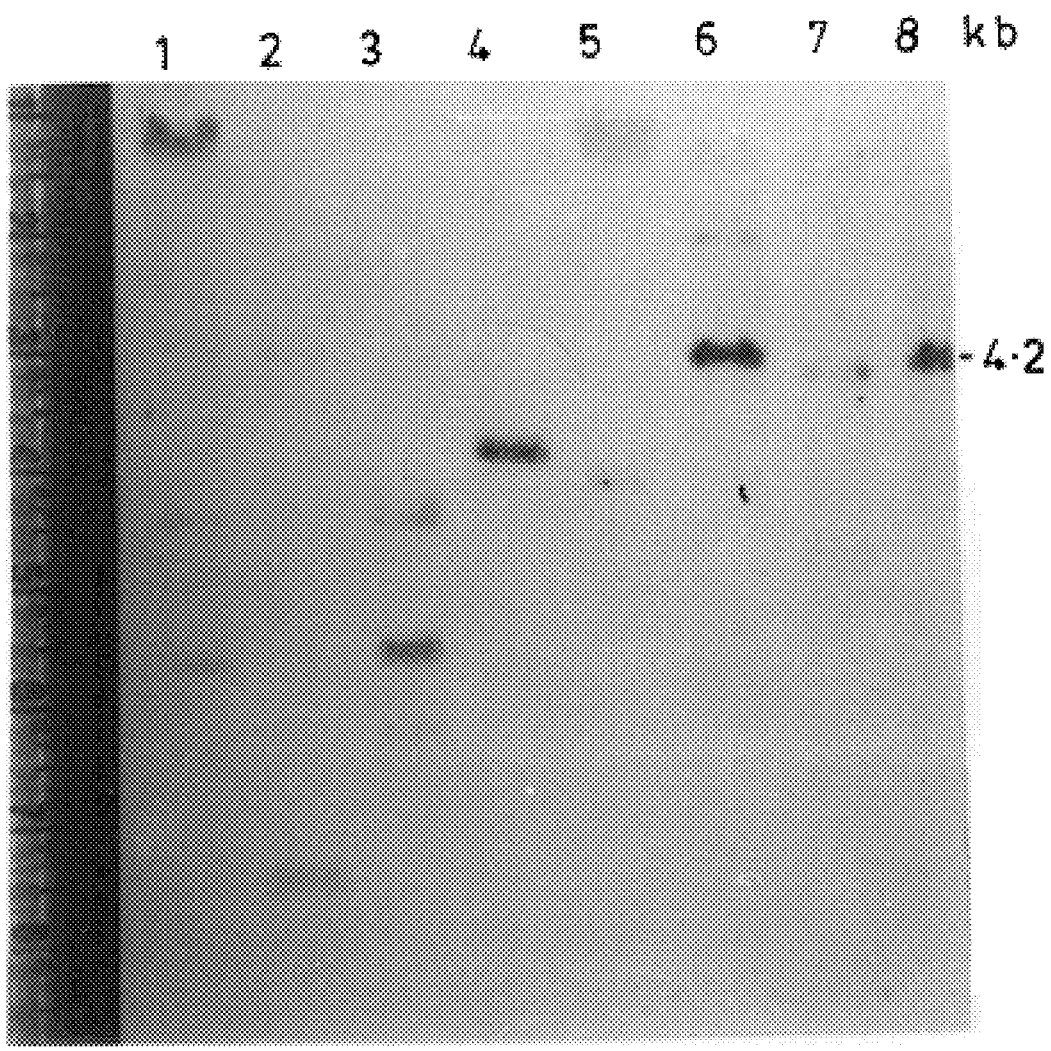
FIG. 3. Southern hybridization of EcoRI digests of recombinant lambda clones with DIG-labeled denatured genomic DNA of Mycobacterium tuberculosis. The recombinant DNA clones shown on the gel is: Lane 1: Clone C70; Lane 2: Clone C60; Lane 3: Clone C41; Lane 4: Clone C38; Lane 5: Clone C33; Lane 6: Clone C16; Lane 7: Clone C10; Lane 8: Clone C8.

The invention is directed to Mycobacterium tuberculosis specific DNA fragment, methods of producing such DNA fragment, characterization of such DNA fragment, nucleotide sequence of such DNA fragment and the use of the DNA fragment or portion thereof for the rapid diagnosis of Mycobacterium tuberculosis infection in clinical samples to identify clinical isolates of Mycobacterium tuberculosis and to monitor the epidemiology of Mycobacterium tuberculosis infection. Specifically, this invention relates to the use of sequence specific DNA fragment to diagnose tuberculosis and strains of Mycobacterium tuberculosis.

The invention relates to production and identification of a DNA fragment which contains an IS like sequence and various repeat sequences unique to Mycobacterium tuberculosis, which is the major etiologic agent of tuberculosis. In particular, it is based on the isolation of Mycobacterium tuberculosis specific DNA fragment containing repetitive sequences using genomic DNA of Mycobacterium tuberculosis as a probe. Repetitive sequences are those which are present in several copies in the genome and give positive hybridization with genomic DNA probe within a short detection period.

As used herein IS like element is intended to refer to an insertion sequence. An insertion sequence is a small, transposable element in bacteria (a small transposon) that can insert into several sites in a genome. Insertion sequences function in the transposition of segments which they flank. They usually contain genes coding for proteins that function in their transposition but contain no other genes and have no other known effect than to function in transposition. The termini of each insertion sequence consist of inverted repeats.

Accordingly, the isolated DNA fragment of Mycobacterium tuberculosis comprises 1291 base pairs, the DNA fragment having following nucleotide sequence (SEQ ID NO:1):

```
AGGCCTCGGT GACCGTGATC ATGTTGCCGC CGAAGGTCAT TACGTTGTGT ACGTCAATGA

CCATCTGCTC GTTGTTTATG GGGATGAATC GGGAGTGGTG ACCGAGAGAT CGATGGCGAA

TCTGGCCCTG GTTATCGCCC GCCACCAAGA AGCCATTGTT GAAGTCGCCC GTGTCGAAAG

CGCCGGTATT GACGTTGCCG GGATTGAAGA AGCCGGTGTT GGTGTCACCC GGGTTATAGC

TGCCGGTATT GGTGTCACCC ACGTTGAAGT TGCCGGTGTT GGTGTTACCG ACGTTGAAGC
```

-continued

```
CGCCGGTGTT GTAGCTGCCC GTGTTGTAGA AGCCCGTGTT GAAGTCGCCG GCGTTGAGGA

TGCCCGTGTT GTAGCTGCCA GCATTGAGGA TGCCGGTATT GTCGGTACCC GGGTTCCCGA

TACCCCAGTT CCCGGTGCCC GAGTTTGCGA TGCCGACGTT TCCGGTGCCC GCGTTGAAGA

TGCCAACGTT ATTGGTGCCC GAATTGAACA GGCCGCTGTT GCCGGTGCCC GAGTTCCAGC
CGCTAGCAAT ATTGAAGCCC TGCTGGTTGT CGCCGGACAG CCCGATGCCG ATGTTGTTGT
TGCCGGTGTT GGCGAACCCG ATGTTGTTGT TGCCGGTGTT GGCAAAGCCT TGGTTGAAGT
CGCCCGCGTT CCCGAAGCCG ACGTTGTAGT CGCCGACGTT TCCAAAACCG ATGTTGTAGA
TCCCGAGGTT TCCGGATCCG ATGTTGTAGT TTCCCAGGCT TCCGGAACCG ACATTGAATA
CTCCGATGTT TCCACTGCCG ATATTGAAGC TGCCGACGTT GCCGCTGCCC AAGATGTTTT
GGCTGCCGAG GTTGCCGCTG CCAAGGATGT TGAAGTCACC GACGTTTCCG CTGCCGAGAA
TGTTGTAATT GCCGATGTTG GCGTTGCCGA GAATGTTCAC GACGCCCCGG TTTGCCAGGC
CGAGATTGAA GACCGGTGGG CCACCGAAAA ATCCCGACAT GTTGCTTCCG GTGTTGAAGA
AGCCCGAGAT CAAGGCCGGC GTTGTGATGG CCACCAGGCT CATGTTGAAC AAACCCGATA
CGGTGTTGCC CGAGTTGATC ACGCCCGATA CCAGCACGCC CGCGTTTGCC AGGCCGGAGT
TACCGATGGC CCCCGACGAA GAGTGGAAGA AGCCAGAATT GTTGGCACCG GAGTTCAGGA
AGCCGGACGC GCTACCGGCA CCGCTGTTGA AGAATCCCGA CGACGGCGCA CTGGTCGAGT
TGAAGAAGCC GGGCTCCCGA AAATCAGGCC T
```

In another embodiment of the invention, there is a process for the production and identification of DNA fragment of *Mycobacterium tuberculosis* comprising 1291 base pairs. One of the processes comprises the following steps:

| | |
|---|---|
| (a) | constructing a library of *Mycobacterium tuberculosis* in a vector including phage lambda gt11 or a plasmid; |
| (b) | screening the genomic library of *Mycobacterium tuberculosis* with genomic DNA of *Mycobacterium tuberculosis* as probe to select DNA fragments capable of specifically and rapidly hybridizing to *Mycobacterium tuberculosis* genomic DNA; |
| (c) | labeling the probe with a label such as digoxigenin, biotin, radiolabelled with $^{32}P$ or alkaline phosphatase; |
| (d) | isolating repetitive DNA fragments with positive hybridization signals ranging between 10 to 60 minutes; and |
| (e) | further screening of the clones isolated above for validation by DNA-DNA hybridization with genomic DNA of mycobacteria other than *Mycobacterium tuberculosis* as probe to confirm that the clone selected above do not produce any hybridization signals with DNA of mycobacteria other than *Mycobacterium tuberculosis*. The DNA fragment identified in this process can be used for the detection of *Mycobacterium tuberculosis* by incubating the isolated DNA fragment with samples which may contain specific mycobacteria (*Mycobacterium tuberculosis*) and detecting the presence or absence of *Mycobacterium tuberculosis*. |

If DNA of *Mycobacterium tuberculosis* is present then the DNA fragment will hybridize with the DNA of *Mycobacterium tuberculosis*.

To produce a sequence specific DNA fragment of *Mycobacterium tuberculosis*, a genomic library of *Mycobacterium tuberculosis* DNA may be constructed in plasmid or phage lambda gt11 vector. The library of genomic fragments may be screened with genomic DNA of *Mycobacterium tuberculosis* as a probe to screen and select DNA fragments which rapidly hybridize to *Mycobacterium tuberculosis* genomic DNA. This may provide DNA fragments which hybridize very rapidly to *Mycobacterium tuberculosis* DNA.

The DNA fragment may be incubated with clinical samples suspected of containing *Mycobacterium tuberculosis* of interest or may be incubated with *Mycobacterium tuberculosis* after it is cultured. If *Mycobacterium tuberculosis* is present, then the specific DNA fragment will hybridize with the DNA of *Mycobacterium tuberculosis* and can be detected by, for example, dot blot or Southern hybridization assay.

The nucleotide sequence of the specific DNA fragment may be determined and specific DNA primers may thus be designed. The so designed primers may be added to the clinical samples. If *Mycobacterium tuberculosis* is present in the clinical samples, the genomic DNA homologous to the specific DNA fragment may be amplified by PCR. The amplified product may be visualized by for example agarose gel electrophoresis and hybridization. The PCR amplification as well as hybridization with the specific DNA fragment of the invention may indicate that the sample contains *Mycobacterium tuberculosis* and hence may be used in detection and diagnosis of tuberculosis. In addition, the specific DNA fragment of the invention may be used to monitor the epidemiology of tuberculosis and strain polymorphism of *Mycobacterium tuberculosis* may be determined.

The method of this invention allows for rapid and specific diagnosis of tuberculosis and *Mycobacterium tuberculosis* infection. The assessment of the diagnosis with the DNA probe of this invention is accurate because the DNA probe owing to its sequence specificity only provides for hybridization and detection of *Mycobacterium tuberculosis* which indicates that the sample contains the mycobacteria of interest i.e. *Mycobacterium tuberculosis*.

The inventors have determined the nucleotide sequence of the DNA fragment of this invention which is 1291 bp long. The nucleotide sequence of the DNA fragment shows several interesting features including the presence of repeat sequences and an IS like sequence with an open reading frame. The IS like sequence is characterized by the presence of two inverted repeats flanked with direct repeat GTT on either side. GTT is a direct repeat which is located at 458 to 460 and at 1193 to 1195.

A section or fragment of the 1291 base pair sequence can also be used to detect *Mycobacterium tuberculosis*.

The deduced amino acid sequence from the nucleotide sequence described in FIG. 9 of the 1291 bp DNA fragment is shown in FIG. 10.

I. Construction of a Recombinant Expression Library of *Mycobacterium tuberculosis* DNA A recombinant DNA expression library of *Mycobacterium tuberculosis* DNA may be constructed using lambda gt11 vector. The library may be constructed with *Mycobacterium tuberculosis* genomic DNA fragments in such a way that all protein coding sequences would be represented and expressed (Young, R. A., B. R. Bloom, C. M. Grosskinsky, J. Ivyani, D. Thomas and R. W. Davis, Proceedings of the National Academy of Sciences, U.S.A., 82:2583–2587 (1985)).

Lambda gt11 is a bacteriophage vector which is capable of driving the expression of foreign insert DNA with *E. coli* transcription and translation signals. Lambda gt11 expresses the insert DNA as a fusion protein connected to the *E. coli* betagalactosidase polypeptide. Lambda gt11 and the *E. coli* strain used (Y1088 and Y1990) have been described previously (Young, R. A. and R. Davis. Proceedings of the National Academy of Sciences, U.S.A., 80:1194–1198, 1983). The techniques of these publications are incorporated herein by reference. The library contained in this manner has a titer of $1\times10^{10}$ pfu/ml. It contains approximately 60% recombinants with an average size of 4 kb.

II. Screening of the Lambda gt11 *Mycobacterium Tuberculosis* Library With Genomic DNA of *Mycobacterium tuberculosis* as Probe Genomic DNA from *Mycobacterium tuberculosis* (*Mycobacterium tuberculosis* H37Rv and confirmed Indian clinical isolates) was used as probe to screen the *Mycobacterium tuberculosis* recombinant DNA library. This work is described below and with specific reference to isolation of repetitive sequences.

The chromosomal DNA from *Mycobacterium tuberculosis* was labeled with digoxigenin and used as a probe. Screening of the lambda genomic library was performed as described in (Sambrook, H., E. F. Fritsch and T. Maniatis. 1989. Molecular Cloning, A Laboratory Manual, 2nd ed. Cold Spring Harbor, N.Y.).

Briefly lambda gt11 recombinants were arrayed on lawn of *E. coli* Y1088. The phages were grown and blotted onto nitrocellulose paper and probed with DIG labeled denatured chromosomal DNA from *Mycobacterium tuberculosis* by DNA hybridization. The signal producing plaques were detected with anti-DIG-alkaline phosphatase labeled antibodies according to the manufacturer's protocol (Boehringer Mannheim, Germany). DNA antibody conjugates were detected by alkaline phosphatase reaction with Nitro Blue tetrazolium (NBT) and 5-Bromo-4-Chloro-3-Indolyl Phosphate (BCIP). The positive hybridization was detected as blue plaque spots. Such signal producing clones were isolated in screen of approximately $6\times10^{4}$ recombinant plaques within 60 minutes of detection time (FIG. 1).

III. Probing of the Arrays of Lambda gt11 DNA Clones With Chromosomal DNA as Probe 0.3 ml of a saturated culture of Y1088 was mixed with recombinant phage (6,000 plaque forming units, pfu) and incubated at 36° C. for 10 minutes. The mixture was added to 3 ml of molten LB soft agar and poured onto 90 mm plates containing 1.5% LB agar and allowed to harden at room temperature for 10 min. The plates were incubated at 37° C. for period at which point clear plaques approximately 1 mm in diameter were visible. The plates were then overlaid with nitrocellulose filters. Subsequent processing of filters for detection of clones containing repetitive sequences was identical to the procedures described for screening of lambda gt11 library with DNA probes (Davis, L. G., M. D. Dibner and J. F. Battey. Basic Methods in Molecular Biology, Elsevier. 1986). The nonradioactive DNA labeling and detection system of Boehringer Mannheim, Germany was used for labeling, hybridization and detection during screening. The amplified library was plated to an approximate $6\times10^3$ pfu per plate using *E. coli* Y1 088 as host strain. Of total 60,000 recombinant plaques, 14 plaques were picked up as a result of tertiary screening with DIG-labeled denatured chromosomal DNA from *Mycobacterium tuberculosis* as a probe. These fourteen plaques gave positive signals within 60 minutes.

The recombinant plaques containing repetitive sequences specific to *Mycobacterium tuberculosis* were isolated by subtractive screening of 14 recombinant plaques with denatured chromosomal DNA from mycobacterial strains other than *Mycobacterium tuberculosis* by DNA hybridization. This resulted in isolation of eight recombinant plaques which hybridized with *Mycobacterium tuberculosis* but not with denatured genomic DNA from *M. avium-intracellulare, M. fortuitum, M. chelonae, M. smegmatis* and *M. pheli.* Theses recombinant plaques were purified, the phage DNA was isolated and digested with EcoRI restriction enzyme to determine the size of the insert DNA in the recombinant plaques (FIG. 2 and Table I). The other set was subjected to Southern blotting and hybridization using DIG labeled denatured genomic DNA from *Mycobacterium tuberculosis.* Positive hybridization was detected within 60 minutes (FIG. 3).

All eight clones contained inserts of different sizes and hybridized with chromosomal DNA of *Mycobacterium tuberculosis.* The insert from clone C8 showed positive hybridization within 10 minutes of detection and was selected for detailed study.

TABLE I

| Recombinant clone | insert fragments (kb) |
|---|---|
| C8 | 4.2* kb |
| C10 | 3.8* kb |
| C16 | 4.2* kb |
| C33 | 2.7* kb |
| C38 | 3.0* kb |
| C41 | 2.4, 1.6*, 1.1, 0.7 kb |
| C60 | 3.8, 2.8, 0.76*, 0.64 kb |
| C70 | 2.4*, 1.6, 1.1, 0.7 kb |

*The fragment(s) which gave positive hybridization signal with DIG-labeled denatured genomic DNA of *Mycobacterium tuberculosis* within 10–60 min.

IV. Recombinant DNA Manipulation

The clone C8 was selected. It contained an insert of 4.2 kb which gave strong hybridization signal within 10 minutes with DIG-labeled denatured chromosomal DNA from *Mycobacterium tuberculosis*. The 4.2 kb DNA fragment from clone C8 was isolated by restriction digestion and subsequent elution of 4.2 kb fragment from the agarose gel. The 4.2 kb fragment was purified and subcloned into pUC13 plasmid vector. The resulting recombinant plasmid was designated as pC8.

V. Localization of Repetitive Sequences Within 1291 bp StuI-StuI DNA Fragment

Figure 4:
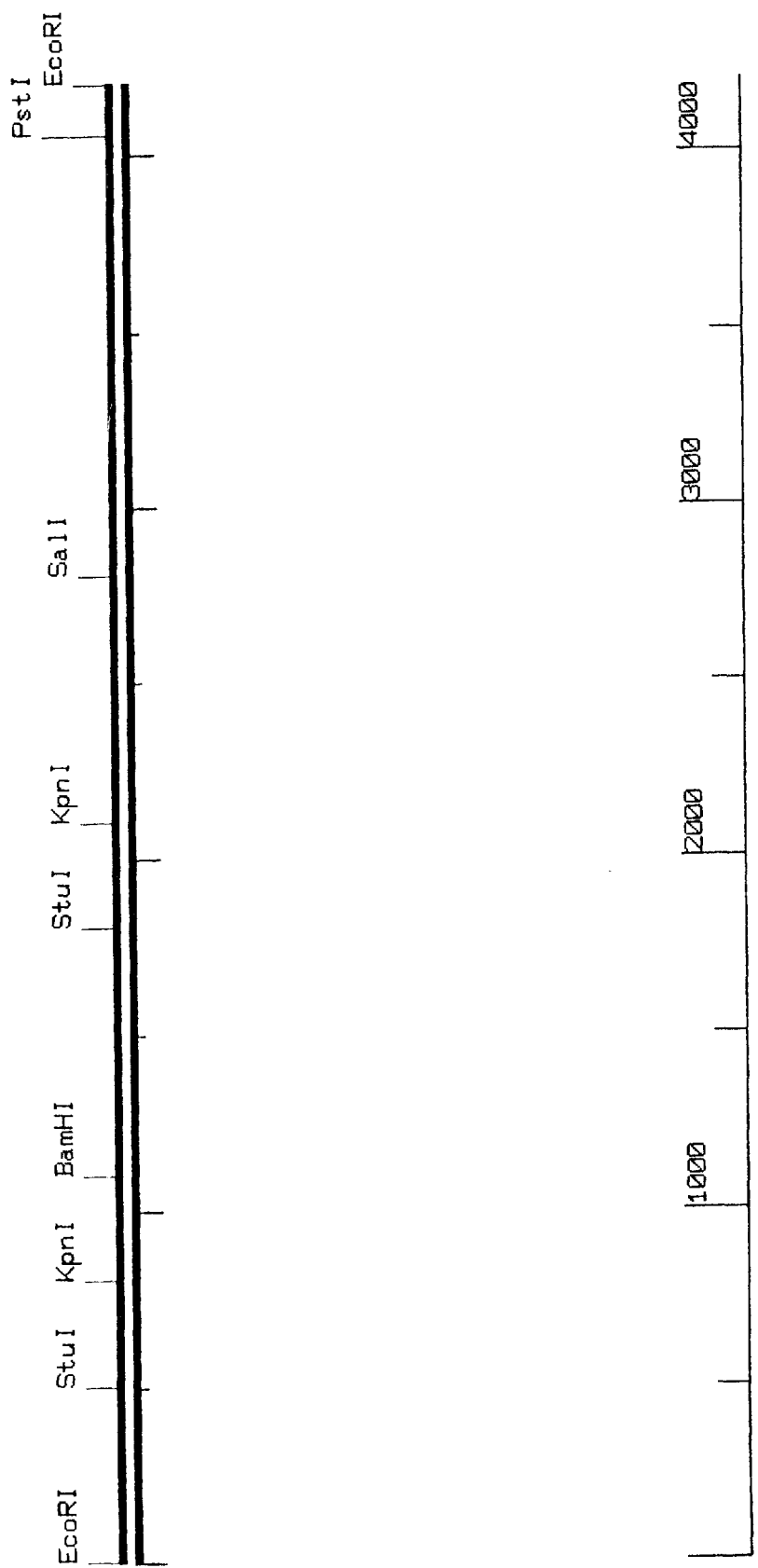
FIG. 4. Restriction map of 4.2 kb DNA fragment of Mycobacterium tuberculosis from Clone C8. The DNA was mapped with restriction endonucleases.

The restriction map of the 4.2 kb DNA fragment was determined (FIG. 4). It contained one site each for BamHI, SalI and two sites each for StuI and KpnI restriction enzymes.

The repetitive sequences within the 4.2 kb DNA fragment were further localized by hybridization of BamHI, SalI, StuI and KpnI restricted fragments of 4.2 kb DNA fragment with DIG-labeled denatured genomic DNA of *Mycobacterium tuberculosis*.

Figure 5:
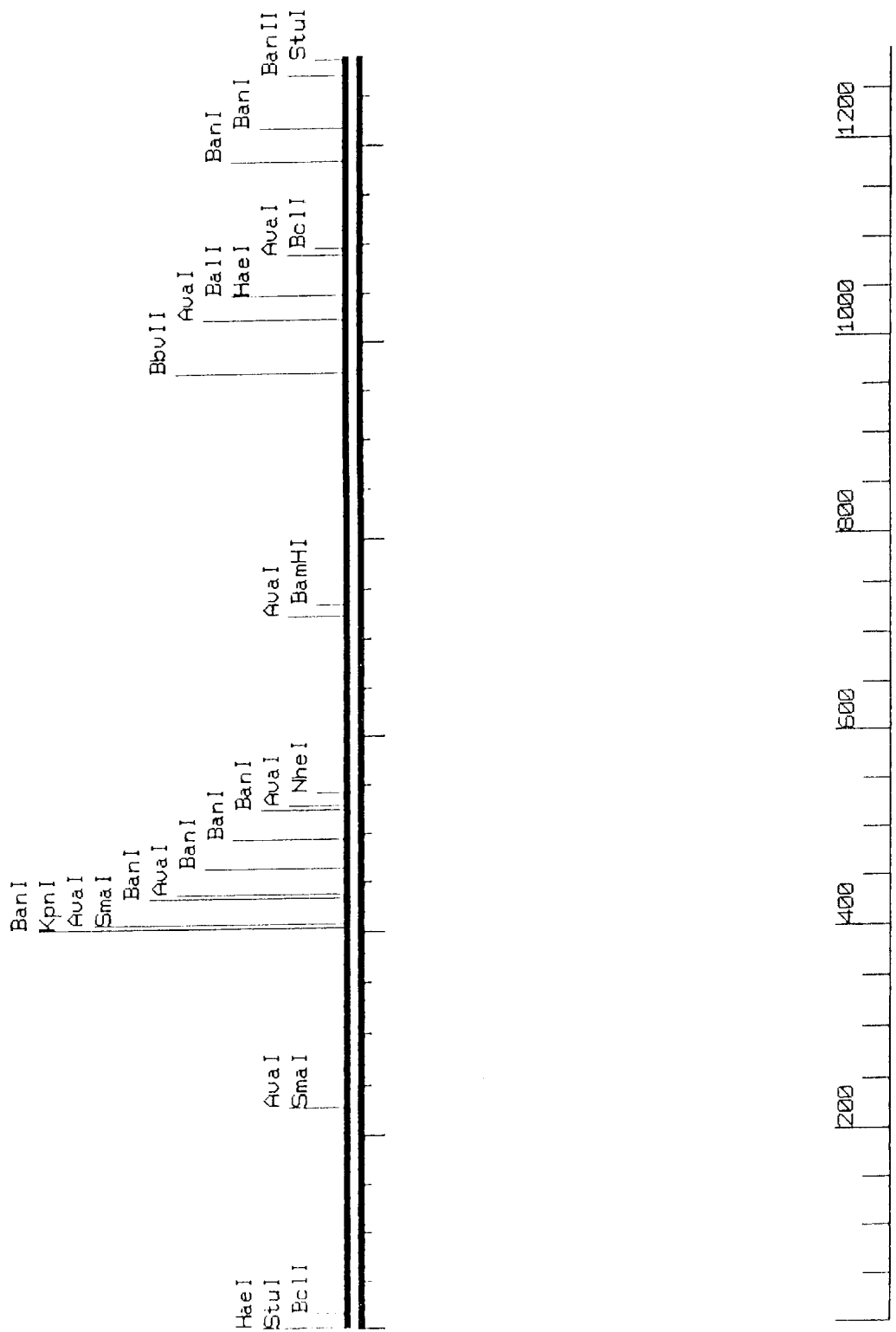
FIG. 5. Restriction map of 1291 bp StuI-StuI fragment of Mycobacterium tuberculosis from clone C8.

The repetitive sequences were localized within StuI-StuI fragment present within 4.2 kb DNA fragment cloned in this invention. The detailed restriction map of StuI-StuI fragment was deduced from the nucleotide sequence of 1291 base pair and confirmed by subsequent digestion with restriction enzymes (FIG. 5).

Figure 6:
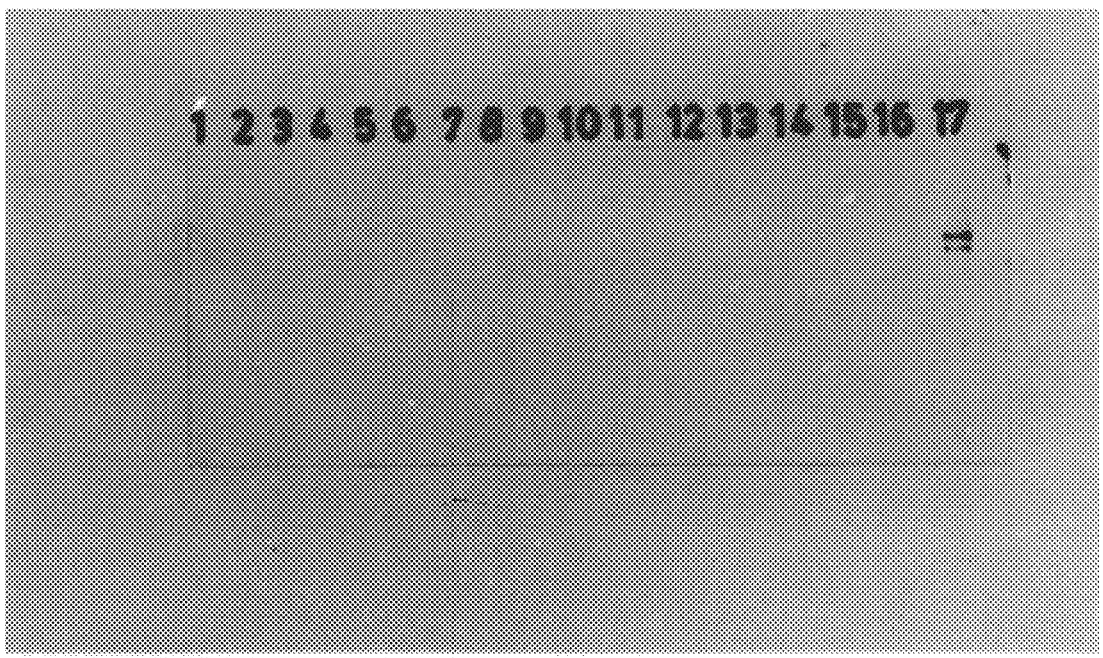
FIG. 6. DNA hybridization of 1291 bp DNA fragment from recombinant clone CD8 with other mycobacterial DNA. Southern hybridization of EcoRI digests of chromosomal DNA of various mycobacterial species (Lanes 1–7) with DIG labeled denatured 1291 bp DNA fragment. Lane 1: *M. smegmatis*; Lane 2: *M. phlei*; Lane 3: *M. avium intracellulare complex;* Lane 4: *M. scrofulaceum;* Lane 5: *M. fortuitum;* Lane 6: *M. kansasii;* Lane 7: *M. gordonae;* Lane 8: *M. asiaticum;* Lane 9: *M. aurum;* Lane 10: *M. chitae;* Lane 11: *M. chelonae;* Lane 12: *M. xenopi;* Lane 13: *M. triviale;* Lane 14: *M. marinum;* Lane 15: *M. microti;* Lane 16: *M. flavescens;* Lane 17: Mycobacterium tuberculosis.

VI. Hybridization of 1291 bp StuI-StuI DNA Fragment With Different Mycobacertial Strains and Other Pathogens The genomic DNA from different mycobacteria and other pathogens was isolated and hybridized with DIG-labeled 1291 bp DNA fragment of pC8 by Southern hybridization as well as dot blot hybridization. As shown in FIG. 6, the fragment did not hybridize in Southern hybridization to the following mycobacterial strains:

*M. smegmatis*
*M. phlei*
*M. fortuitum*
*M. chelonae*
*M. flavescens*
*M. chelonae*
*M. trivale*
*M. duvali*
*M. marinum*
*M. gordonae*
*M. kansasii*
*M. avium*
*M. intracellulare*
*M. scrofulaceum*
*M. gordonae*
*M. xenopi*
*M. aurum*
*M. microti*
*M. szulgai*

The genomic DNA from the above mentioned bacteria were isolated and digested with EcoRI restriction enzyme. The digest was electrophoresed in 0.8% agarose gel, blotted onto nitrocellulose paper and hybridized with DIG-labeled denatured 1291 bp DNA fragment as a probe. The Southern hybridization of 1291 bp fragment with genomic DNA of *Mycobacterium tuberculosis* revealed several bands confirming the presence of repetitive sequences with 1291 bp DNA fragment whereas no hybridization was found with the other mycobacteria listed above (FIG. 6).

The hybridization of 1291 bp DNA fragment was done with genomic DNA from other pathogenic organisms listed below. The result of dot blot hybridization is shown in FIG. 7.

*Salmonella typhimurium*
*Staphylococcus aureus*
*Proteus vulgaris*
*Pseudomonas aeruginosa*
*Klebsiella pneumoniae*
*Enterobacter alginii*
*Vibrio cholerae*
*Bacillus subtilis*
*Edwardsiella*
*Salmon sperm DNA*
*Human placental DNA*
*E. coli*

Figure 7:
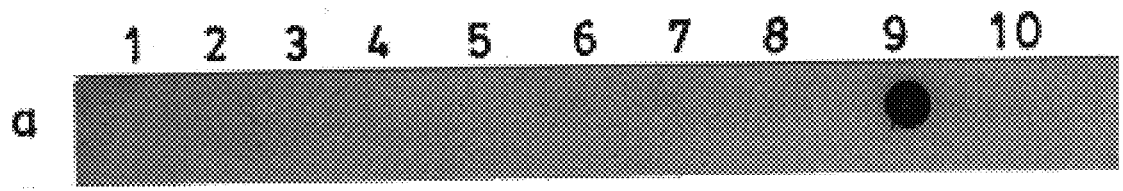
FIG. 7. Dot-blot hybridization of non-mycobacterial DNA with DIG-labeled denatured 1291 bp DNA fragment. 1. *Salmonella typhimurium;* 2. *Enterobacter alginii;* 3. *Klebsiella pneumoniae;* 4. *Pseudomonas aeruginosa;* 5. *Proteus vulgaris;* 6. *Staphylococcus aureus;* 7. *Escherichia coli;* 8. *Edwardsiella sp.;* 9. *Mycobacterium tuberculosis;* 10. Human placental DNA.

The 1291 bp DNA fragment did not hybridize to the genomic DNA of these pathogens (FIG. 7).

VII. Hybridization of 1291 bp StuI-StuI DNA Fragment With Clinical Isolates of *Mycobacterium tuberculosis*

The Southern hybridization of 1291 bp DNA fragment with genomic DNA of clinical isolates of *Mycobacterium tuberculosis* should permit the detection of this 1291 bp DNA fragment in *Mycobacterium tuberculosis* and its use in epidemiology.

Figure 8:
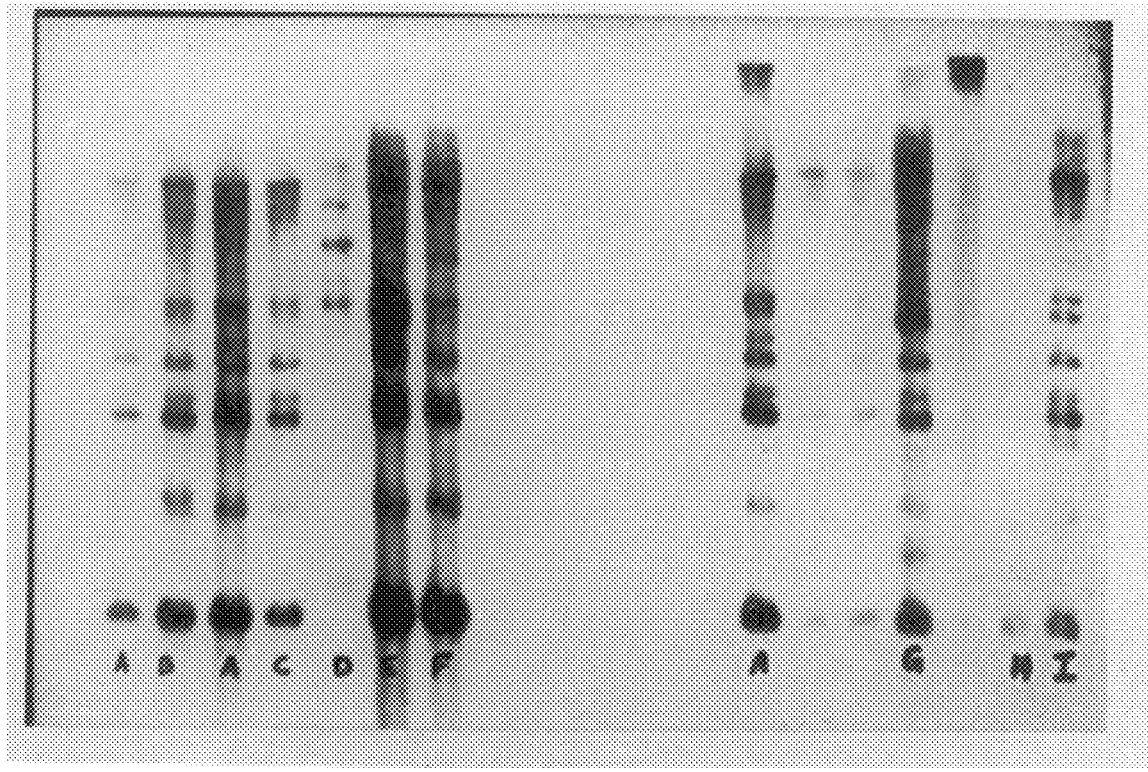
FIG. 8. DNA hybridization of 1291 bp StuI-StuI fragment with StuI digested genomic DNA of clinical isolates of Mycobacterium tuberculosis.

The genomic DNA from confirmed clinical isolates of *Mycobacterium tuberculosis* were isolated and digested with StuI restriction enzyme. The digests were electrophoresed, transferred onto nitrocellulose paper and hybridized with DIG-labeled denatured 1291 bp DNA fragment. The results with more than two hundred clinical isolates of *Mycobacterium tuberculosis* showed the presence of this fragment. The hybridization revealed several bands which confirmed the repetitive nature of the fragment. Several isotopes were identified, however all the isolates showed a strong band of 1291 bp (FIG. 8).

VIII. Nucleotide Sequence of 1291 bp StuI-StuI DNA Fragment

The nucleotide sequence of 1291 bp DNA fragment was determined by dideoxy chain termination sequencing technique (Biggin, M. D. et al. 1983. Proceedings of the National Academy of Sciences, U.S.A. 80:3963–3965). The products of the sequencing reactions were electrophoresed on 6% acrylamide/7M. urea/0.5–2.5×TBE gradient sequencing gels. The gels were dried under vacuum and exposed to Kodak XRP-1 film. The nucleotide sequences were determined independently for both strands of 1291 bp DNA fragment. Computer-aided analysis of the nucleotide sequence and deduced protein sequence was performed using databases and programs provided by the National Institute of Health, as well as the programs of Chou and Fasman and Hopp and Woods. (Chou, P. Y. and G. D. Fasman, Advances in Enzymol., 47:45–148, 1978; Hopp, T. P. and K. P. Woods, Proceedings of the National Academy of Sciences, U.S.A., 78:3824–3828, 1981). The nucleotide sequence of the 1291 bp StuI-StuI region of 4.2 kb DNA fragment is represented in FIG. 9. The nucleotide sequence of the DNA fragment shows several interesting features including the presence of repeat sequences and an IS like sequence with open reading frame. The nucleotide sequence of the DNA fragment of this invention along with IS and repeat sequences present within the sequence can be seen in FIG. 9. In Table II, the presence of direct repeats in 1291 bp StuI-StuI DNA fragment is shown. Only 10 repeats of more than 9 nucleotide bases along with the sequence and their position have been shown. In Table III, the presence of hairpin loop site in IS like element present within 1291 bp StuI-StuI DNA fragment has been shown. The two inverted repeats are flanked with direct repeat GTT on either side.

TABLE II

The presence of Direct repeats in 1291 bp StuI-StuI DNA fragment

| S.N. | Length (bp) | Sequence | Position | SEQ ID NO 1 |
|---|---|---|---|---|
| 1. | 26 | CCG ATG TTG TTG TTG CCG GTG TTG GC | 588, 618 | SEQ ID NO: 31 |
| 2. | 10 | TGA AGA AGC C | 205, 1015, 1261 | SEQ ID NO: 41 |
| 3. | 10 | GCC CGT GTT G | 317, 332, 362 | SEQ ID NO: 51 |
| 4. | 10 | TTG AGG ATG C | 354, 384 | SEQ ID NO: 61 |
| 5. | 9 | CCG GTG TTG | 213, 273, 303, 603 | |
| 6. | 9 | CCG ATG TTG | 588, 618, 708, 738, 912 | |
| 7. | 9 | GTT GAA GTC | 158, 338, 653, 869 | |
| 8. | 9 | GAA GAA GCC | 206, 1016, 1166, 1262 | |
| 9. | 9 | GTT GCC GGT | 269, 518, 599, 629 | |
| 10. | 9 | GCC GAC GTT | 452, 677, 692, 812 | |

TABLE III

Presence of hairpin loop site in IS like element present within 1291 bp StuI-StuI fragment

| No. | Stem length (bp) | % | Loop length | Hairpin loop sequence (SEQ ID NO: 71) |
|---|---|---|---|---|
| 1. | 9 | 100 | 714 | 461      469      475<br>.        .        .<br>5' TCCGGTGCCCGCGTT.......<br>...........<br>...........       .<br>3' AGGCCACGGTTGTTA.......<br>.        .        .<br>1192    1184    1178 |

* continuation of sequence

The inverted repeats are located at 461 to 469 (TCCGGTGCC) and at 1184 to 1192 (GGCACCGGA).

We claim:

1. An isolated DNA fragment of *Mycobacterium tuberculosis* comprising 1291 base pairs, the DNA fragment having the nucleotide sequence of SEQ ID NO:1.

2. A DNA fragment of *Mycobacterium tuberculosis* as claimed in claim 1, wherein said DNA fragment codes for an amino acid sequence of SEQ ID NO:2.

3. A DNA fragment of *Mycobacterium tuberculosis* as claimed in claim 1, wherein said DNA fragment comprises repetitive sequences identified as SEQ ID NO:3; SEQ ID NO:4; SEQ ID NO:5; SEQ ID NO:6; and repetitive sequences CCG GTG TTG; CCG ATG TTG; GTT GAA GTC; GAA GAA GCC; GTT GCC GGT; and GCC GAC GTT.

4. A DNA fragment of *Mycobacterium tuberculosis* as claimed in claim 1 having an IS like element.

5. A DNA fragment of *Mycobacterium tuberculosis* as claimed in claim 4, having an IS like sequence of SEQ ID NO:7.

* * * * *

SEQUENCE LISTING

<160> NUMBER OF SEQ ID NOS: 7

<210> SEQ ID NO 1
<211> LENGTH: 1291
<212> TYPE: DNA
<213> ORGANISM: Mycobacterium tuberculosis

<400> SEQUENCE: 1

```
aggcctcggt gaccgtgatc atgttgccgc cgaaggtcat tacgttgtgt acgtcaatga      60
ccatctgctc gttgtttatg gggatgaatc gggagtggtg accgagagat cgatggcgaa     120
tctggccctg gttatcgccc gccaccaaga agccattgtt gaagtcgccc gtgtcgaaag     180
cgccggtatt gacgttgccg ggattgaaga agccggtgtt ggtgtcaccc gggttatagc     240
tgccggtatt ggtgtcaccc acgttgaagt tgccggtgtt ggtgttaccg acgttgaagc     300
cgccggtgtt gtagctgccc gtgttgtaga agcccgtgtt gaagtcgccg gcgttgagga     360
tgcccgtgtt gtagctgcca gcattgagga tgccggtatt gtcggtaccc gggttcccga     420
taccccagtt cccggtgccc gagtttgcga tgccgacgtt tccggtgccc gcgttgaaga     480
tgccaacgtt attggtgccc gaattgaaca ggccgctgtt gccggtgccc gagttccagc     540
cgctagcaat attgaagccc tgctggttgt cgccggacag cccgatgccg atgttgttgt     600
tgccggtgtt ggcgaacccg atgttgttgt tgccggtgtt ggcaaagcct tggttgaagt     660
cgcccgcgtt cccgaagccg acgttgtagt cgccgacgtt tccaaaaccg atgttgtaga     720
tcccgaggtt tccggatccg atgttgtagt ttcccaggct tccggaaccg acattgaata     780
ctccgatgtt tccactgccg atattgaagc tgccgacgtt gccgctgccc aagatgtttt     840
ggctgccgag gttgccgctg ccaaggatgt tgaagtcacc gacgtttccg ctgccgagaa     900
tgttgtaatt gccgatgttg gcgttgccga gaatgttcac gacgcccggg tttgccaggc     960
cgagattgaa gaccggtggg ccaccgaaaa atcccgacat gttgcttccg gtgttgaaga    1020
agcccgagat caaggccggc gttgtgatgg ccaccaggct catgttgaac aaacccgata    1080
cggtgttgcc cgagttgatc acgcccgata ccagcacgcc cgcgtttgcc aggccggagt    1140
taccgatggc ccccgacgaa gagtggaaga agccagaatt gttggcaccg gagttcagga    1200
agccggacgc gctaccggca ccgctgttga agaatcccga cgacggcgca ctggtcgagt    1260
tgaagaagcc gggctcccga aaatcaggcc t                                   1291
```

<210> SEQ ID NO 2
<211> LENGTH: 430
<212> TYPE: PRT
<213> ORGANISM: Mycobacterium tuberculosis
<220> FEATURE:
<221> NAME/KEY: UNSURE
<222> LOCATION: (4)
<220> FEATURE:
<221> NAME/KEY: UNSURE
<222> LOCATION: (6)
<220> FEATURE:
<221> NAME/KEY: UNSURE
<222> LOCATION: (20)
<220> FEATURE:
<221> NAME/KEY: UNSURE
<222> LOCATION: (29)
<220> FEATURE:
<221> NAME/KEY: UNSURE -continued

```
<222> LOCATION: (54)
<220> FEATURE:
<221> NAME/KEY: UNSURE
<222> LOCATION: (64)
<220> FEATURE:
<221> NAME/KEY: UNSURE
<222> LOCATION: (69)
<220> FEATURE:
<221> NAME/KEY: UNSURE
<222> LOCATION: (89)
<220> FEATURE:
<221> NAME/KEY: UNSURE
<222> LOCATION: (99)
<220> FEATURE:
<221> NAME/KEY: UNSURE
<222> LOCATION: (114)
<220> FEATURE:
<221> NAME/KEY: UNSURE
<222> LOCATION: (119)
<220> FEATURE:
<221> NAME/KEY: UNSURE
<222> LOCATION: (129)
<220> FEATURE:
<221> NAME/KEY: UNSURE
<222> LOCATION: (159)
<220> FEATURE:
<221> NAME/KEY: UNSURE
<222> LOCATION: (169)
<220> FEATURE:
<221> NAME/KEY: UNSURE
<222> LOCATION: (182)
<220> FEATURE:
<221> NAME/KEY: UNSURE
<222> LOCATION: (185)
<220> FEATURE:
<221> NAME/KEY: UNSURE
<222> LOCATION: (219)
<220> FEATURE:
<221> NAME/KEY: UNSURE
<222> LOCATION: (259)
<220> FEATURE:
<221> NAME/KEY: UNSURE
<222> LOCATION: (269)
<220> FEATURE:
<221> NAME/KEY: UNSURE
<222> LOCATION: (291)
<220> FEATURE:
<221> NAME/KEY: UNSURE
<222> LOCATION: (323)
<220> FEATURE:
<221> NAME/KEY: UNSURE
<222> LOCATION: (339)
<220> FEATURE:
<221> NAME/KEY: UNSURE
<222> LOCATION: (349)
<220> FEATURE:
<221> NAME/KEY: UNSURE
<222> LOCATION: (356)
<220> FEATURE:
<221> NAME/KEY: UNSURE
<222> LOCATION: (366)
<220> FEATURE:
<221> NAME/KEY: UNSURE
<222> LOCATION: (410)
<220> FEATURE:
<221> NAME/KEY: UNSURE
<222> LOCATION: (421)

<400> SEQUENCE: 2

Arg Pro Arg Xaa Pro Xaa Ser Cys Cys Arg Arg Ser Leu Arg Cys
 1               5                  10                  15

Val Arg Gln Xaa Pro Ser Ala Arg Cys Leu Trp Gly Xaa Ile Gly Ser
            20                  25                  30

Gly Asp Arg Glu Ile Asp Gly Ser Gly Pro Gly Tyr Arg Pro Pro
        35                  40                  45
```

```
Pro Arg Ser His Cys Xaa Ser Arg Pro Cys Arg Lys Arg Arg Tyr Xaa
        50                  55                  60

Arg Cys Arg Asp Xaa Arg Ser Arg Cys Trp Cys His Pro Gly Tyr Ser
 65                  70                  75                  80

Cys Arg Tyr Trp Cys His Pro Arg Xaa Ser Cys Arg Cys Trp Cys Tyr
                 85                  90                  95

Arg Arg Xaa Ser Arg Arg Cys Cys Ser Cys Pro Cys Cys Arg Ser Pro
            100                 105                 110

Cys Xaa Ser Arg Arg Xaa Gly Cys Pro Cys Cys Ser Cys Gln His
        115                 120                 125

Xaa Gly Cys Arg Tyr Cys Arg Tyr Pro Gly Ser Arg Tyr Pro Ser Ser
        130                 135                 140

Arg Cys Pro Ser Leu Arg Cys Arg Arg Phe Arg Cys Pro Arg Xaa Arg
145                 150                 155                 160

Cys Gln Arg Tyr Trp Cys Pro Asn Xaa Thr Gly Arg Cys Cys Arg Cys
                165                 170                 175

Pro Ser Ser Ser Arg Xaa Gln Tyr Xaa Ser Pro Ala Gly Cys Arg Arg
            180                 185                 190

Thr Ala Arg Cys Arg Cys Cys Cys Arg Cys Trp Arg Thr Arg Cys
        195                 200                 205

Cys Cys Cys Arg Cys Trp Gln Ser Leu Gly Xaa Ser Arg Pro Arg Ser
210                 215                 220

Arg Ser Arg Arg Cys Ser Arg Arg Phe Gln Asn Arg Cys Arg
225                 230                 235                 240

Ser Arg Gly Phe Arg Ile Arg Cys Cys Ser Phe Pro Gly Phe Arg Asn
            245                 250                 255

Arg His Xaa Ile Leu Arg Cys Phe His Cys Arg Tyr Xaa Ser Cys Arg
        260                 265                 270

Arg Cys Arg Cys Arg Arg Cys Phe Gly Cys Arg Gly Cys Arg Cys Gln
        275                 280                 285

Gly Cys Xaa Ser His Arg Arg Phe Arg Cys Arg Glu Cys Cys Asn Cys
        290                 295                 300

Arg Cys Trp Arg Cys Arg Glu Cys Ser Arg Arg Pro Gly Leu Pro Gly
305                 310                 315                 320

Arg Asp Xaa Arg Pro Val Gly His Arg Lys Ile Pro Thr Cys Cys Phe
                325                 330                 335

Arg Cys Xaa Arg Ser Pro Arg Ser Arg Pro Ala Leu Xaa Trp Pro Pro
            340                 345                 350

Gly Ser Cys Xaa Thr Asn Pro Ile Arg Cys Cys Pro Ser Xaa Ser Arg
            355                 360                 365

Pro Ile Pro Ala Arg Pro Arg Leu Pro Gly Arg Ser Tyr Arg Trp Pro
370                 375                 380

Pro Thr Lys Ser Gly Arg Ser Gln Asn Cys Trp His Arg Ser Ser Gly
385                 390                 395                 400

Ser Arg Thr Arg Tyr Arg His Arg Cys Xaa Arg Ile Pro Thr Thr Ala
                405                 410                 415

His Trp Ser Ser Xaa Arg Ser Arg Ala Pro Glu Asn Gln Ala
            420                 425                 430

<210> SEQ ID NO 3
<211> LENGTH: 26
<212> TYPE: DNA
<213> ORGANISM: Mycobacterium tuberculosis

<400> SEQUENCE: 3
```

-continued

```
ccgatgttgt tgttgccggt gttggc                                           26

<210> SEQ ID NO 4
<211> LENGTH: 10
<212> TYPE: DNA
<213> ORGANISM: Mycobacterium tuberculosis

<400> SEQUENCE: 4
tgaagaagcc                                                             10

<210> SEQ ID NO 5
<211> LENGTH: 10
<212> TYPE: DNA
<213> ORGANISM: Mycobacterium tuberculosis

<400> SEQUENCE: 5
gcccgtgttg                                                             10

<210> SEQ ID NO 6
<211> LENGTH: 10
<212> TYPE: DNA
<213> ORGANISM: Mycobacterium tuberculosis

<400> SEQUENCE: 6
ttgaggatgc                                                             10

<210> SEQ ID NO 7
<211> LENGTH: 732
<212> TYPE: DNA
<213> ORGANISM: Mycobacterium tuberculosis

<400> SEQUENCE: 7
tccggtgccc gcgttgaaga tgccaacgtt attggtgccc gaattgaaca ggccgctgtt       60
gccggtgccc gagttccagc cgctagcaat attgaagccc tgctggttgt cgccggacag      120
cccgatgccg atgttgttgt tgccggtgtt ggcgaacccg atgttgttgt tgccggtgtt      180
ggcaaagcct tggttgaagt cgcccgcgtt cccgaagccg acgttgtagt cgccgacgtt      240
tccaaaaccg atgttgtaga tcccgaggtt tccggatccg atgttgtagt ttcccaggct      300
tccggaaccg acattgaata ctccgatgtt tccactgccg atattggagc tgccgacgtt      360
gccgctgccc aagatgtttt ggctgccgag gttgccgctg ccaaggatgt tgaagtcacc      420
gacgtttccg ctgccgagaa tgttgtaatt gccgatgttg gcgttgccga gaatgttcac      480
gacgccccgg tttgccaggc cgagattgaa gaccggtggg ccaccgaaaa atcccgacat      540
gttgcttccg gtgttgaaga agcccgagat caaggccggc gttgtgatgg ccaccaggct      600
```

-continued

```
catgttgaac aaacccgata cggtgttgcc cgagttgatc acgcccgata ccagcacgcc    660
cgcgtttgcc aggccggagt taccgatggc ccccgacgaa gagtggaaga agccagaatt    720
gttggcaccg ga                                                        732
```